(12) United States Patent
Pischlar et al.

(10) Patent No.: US 12,115,380 B2
(45) Date of Patent: Oct. 15, 2024

(54) MEDICAL DEVICE WITH BRAIDED TUBULAR BODY

(71) Applicant: Medtronic, Inc., Minneapolis, MN (US)

(72) Inventors: Jesse J. Pischlar, St. Paul, MN (US); Kenneth C. Gardeski, Plymouth, MN (US); Michael R. Leners, St. Francis, MN (US); Peter B. McIntyre, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 99 days.

(21) Appl. No.: 17/062,534

(22) Filed: Oct. 2, 2020

(65) Prior Publication Data

US 2021/0106838 A1  Apr. 15, 2021

Related U.S. Application Data

(60) Provisional application No. 62/913,833, filed on Oct. 11, 2019.

(51) Int. Cl.
*A61N 1/04* (2006.01)
*A61N 1/375* (2006.01)
*A61N 1/39* (2006.01)

(52) U.S. Cl.
CPC ....... *A61N 1/39622* (2017.08); *A61N 1/0472* (2013.01); *A61N 1/0488* (2013.01); *A61N 1/37512* (2017.08); *A61N 1/3754* (2013.01)

(58) Field of Classification Search
None
See application file for complete search history.

(56) References Cited

U.S. PATENT DOCUMENTS

| | | | | |
|---|---|---|---|---|
| 5,796,044 | A * | 8/1998 | Cobian | A61N 1/056 174/113 AS |
| 8,676,347 | B2 | 3/2014 | Finley et al. | |
| 8,788,061 | B2 * | 7/2014 | Mehdizadeh | A61N 1/056 607/115 |
| 9,659,679 | B2 | 5/2017 | McIntyre et al. | |
| 2003/0216800 | A1 * | 11/2003 | Ebert | A61N 1/056 607/122 |
| 2007/0255255 | A1 * | 11/2007 | Shah | A61M 25/005 604/527 |

(Continued)

FOREIGN PATENT DOCUMENTS

WO    2017/180832    10/2017

OTHER PUBLICATIONS

International Search Report and Written Opinion for PCT Application No. PCT/US2020/054709, dated Jan. 27, 2021, 10 pages.

*Primary Examiner* — Eugene T Wu
(74) *Attorney, Agent, or Firm* — Mueting Raasch Group (57) ABSTRACT

A medical device includes an elongated body having a proximal end and a distal end and a braided tubular body extending coaxially with the elongated body between the proximal and distal ends. The braided tubular body includes multiple cables extending helically in opposing directions in an interwoven manner. Each cable includes multiple, electrically conductive filars. In some examples, each filar includes an electrically insulating coating or layer.

20 Claims, 7 Drawing Sheets

(56) References Cited

U.S. PATENT DOCUMENTS

| | | | |
|---|---|---|---|
| 2010/0160989 A1* | 6/2010 | Legay | A61N 1/3931 607/63 |
| 2010/0174348 A1* | 7/2010 | Bulkes | A61N 1/05 607/116 |
| 2011/0054584 A1* | 3/2011 | Alexander | A61N 1/0551 607/116 |
| 2012/0041528 A1 | 2/2012 | Mehdizadeh et al. | |
| 2012/0110846 A1* | 5/2012 | Franz | A61N 1/0551 29/876 |
| 2013/0304160 A1* | 11/2013 | Gunderson | A61N 1/372 607/66 |
| 2014/0018895 A1* | 1/2014 | Geroy | A61N 1/0551 607/116 |
| 2015/0314123 A1 | 11/2015 | Sharma et al. | |
| 2017/0080213 A1* | 3/2017 | Wright | A61N 1/0551 |

* cited by examiner

MEDICAL DEVICE WITH BRAIDED TUBULAR BODY

RELATED APPLICATIONS

The present application claims the benefit of U.S. Provisional Application No. 62/913,833, filed Oct. 11, 2019, which is incorporated herein by reference in its entirety.

TECHNICAL FIELD

This disclosure relates to a medical device having an elongated tubular body including braided multi-filar cables.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscles, nerves, brain, stomach or other organs or tissue of a patient. Some medical devices may employ one or more electrodes for the delivery of therapeutic electrical signals to such organs or tissues and/or one or more electrodes for sensing intrinsic electrical signals within the patient that are generated by such organs or tissue. Similarly, some medical devices may additionally or alternatively include one or more other sensors for sensing physiological parameters of a patient.

For example, some medical devices may function as cardiac pacemakers or cardioverter-defibrillators that provide therapeutic electrical signals to the heart. The therapeutic electrical signals may include pulses for pacing, or shocks for cardioversion or defibrillation. In some examples, a medical device may sense intrinsic cardiac electrical signals attendant to depolarizations of the heart and thereby control delivery of therapeutic signals to the heart based on the sensed signals. Upon detection of an abnormal rhythm, such as bradycardia, tachycardia, or fibrillation, an appropriate therapeutic electrical stimulation pulse or pulses may be delivered to restore or promote a relatively more normal heart rhythm. For example, in some cases, an implanted medical device may deliver pacing stimulation to the heart of the patient upon detecting tachycardia or bradycardia, and/or deliver cardioversion or defibrillation shocks to the heart upon detecting fibrillation.

In some examples a medical device may utilize one or more medical leads with one or more electrodes or other sensors for delivery of therapeutic electrical signals or for sensing physiological signals. For example, electrodes or sensors may be carried at a distal portion of a lead, where, a proximal portion of the lead may be coupled to a medical device housing that contains circuitry such as electrical pulse generation and/or sensing circuitry.

In other examples, medical monitoring and/or therapy delivery may require the use of an elongated catheter or tubular body to deliver electrical stimulation signals, e.g., cardiac ablation signals, nerve ablation signals and/or sense electrical signals, e.g., produced by a patient's heart or other muscles or nerves. In some cases, a tubular catheter may be used as delivery tool for delivering an implantable medical device such as a leadless cardiac pacemaker, to a target implant site within a patient's heart.

SUMMARY

The techniques of this disclosure generally relate to elongated medical devices used in delivering a therapy and/or monitoring physiological signals of a patient. An elongated medical device according to this disclosure includes multi-filar cables braided together in an elongated braided tubular body. Each multi-filar cable includes two or more individual filars, and the multiple multi-filar cables wind helically in opposing directions around a central axis of the elongated medical device, in an interwoven, overlapping manner. The medical device may be a medical electrical lead or a catheter, as examples. The braided tubular body may be configured to conduct electrical signals between a proximal end and distal end of the elongated medical device, e.g., between a distal electrode or sensor and a proximal electrical connector.

According to one example, the disclosure provides a medical device including an elongated tubular body having a proximal end, a distal end and a central axis. The device further includes a braided tubular body extending between the proximal end and the distal end of the elongated tubular body. The braided tubular body includes a first plurality of cables winding in a first direction around the central axis of the elongated tubular body and a second plurality of cables winding in a second direction opposite the first direction around the central axis of the elongated tubular body. At least a portion of the first plurality of cables and the second plurality of cables are multi-filar cables, each multi-filar cable including multiple filars.

In another example, the disclosure provides an implantable medical electrical lead including an elongated tubular body having a proximal end, a distal end and a central axis. The lead further includes an electrode carried by the elongated tubular body, a proximal electrical connector coupled to the proximal end of the elongated tubular body, and a braided tubular body extending between the proximal end and the distal end of the elongated tubular body. The braided tubular body includes a first plurality of cables winding in a first direction around the central axis of the elongated tubular body and a second plurality of cables winding in a second direction opposite the first direction around the central axis of the elongated tubular body. At least a portion of the first plurality of cables and the second plurality of cables are multi-filar cables, each multi-filar cable including multiple electrically conductive filars. At least a portion of the multi-filar cables are electrically coupled to the electrode and to the proximal electrical connector.

In another example, the disclosure provides an implantable catheter including an elongated tubular body having a proximal end, a distal end and a central axis, an electrode carried by the elongated tubular body and a proximal electrical connector coupled to the proximal end of the elongated tubular body. The catheter further includes a braided tubular body extending between the proximal end and the distal end of the elongated tubular body. The braided tubular body includes a first plurality of cables winding in a first direction around the central axis of the elongated tubular body and a second plurality of cables winding in a second direction opposite the first direction around the central axis of the elongated tubular body. At least a portion of the first plurality of cables and the second plurality of cables are multi-filar cables. Each multi-filar cable includes multiple electrically conductive filars. At least a portion of the multi-filar cables are electrically coupled to the electrode and to the proximal electrical connector.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

An elongated medical device is disclosed herein including a braided tubular body of multi-filar cables. The braided tubular body may provide mechanical reinforcement along at least a portion of the elongated medical device. The multi-filar cables may be electrically conductive such that the braided tubular body may provide an electrically conductive pathway between proximal and distal ends of the elongated medical device for delivering electrical signals and/or sensing electrical signals, e.g., produced by the heart, muscle, brain or nerves.

Figure 1:
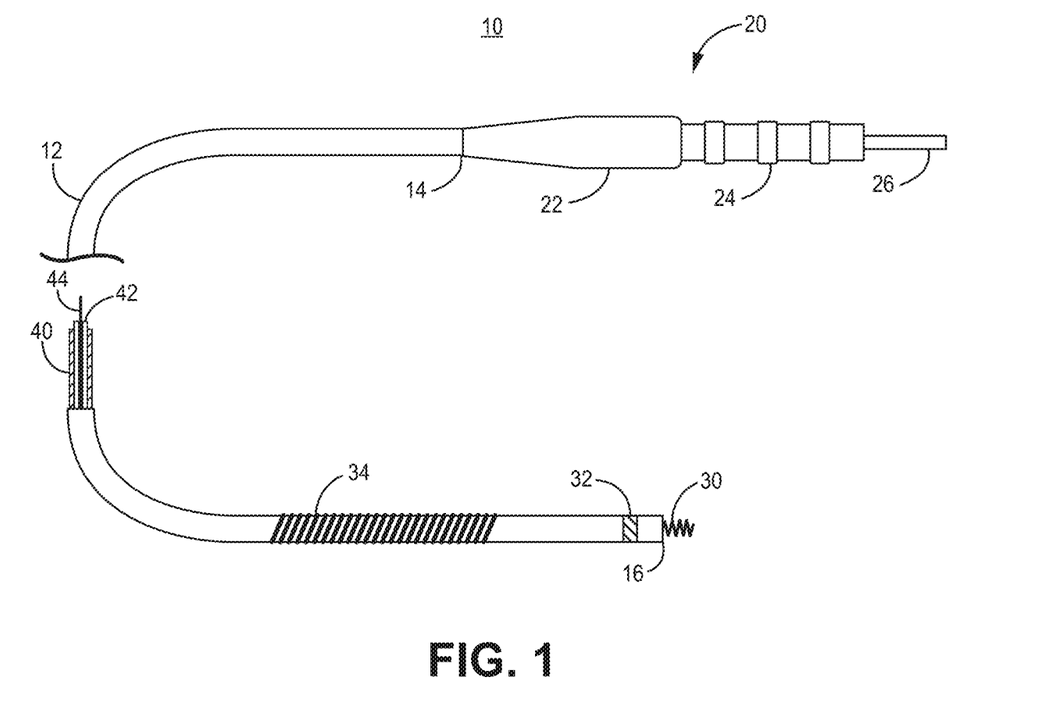
FIG. 1 is a conceptual diagram of an elongated medical device including a braided tubular body according to one example.

FIG. 1 is a conceptual diagram of an elongated medical device 10 including an electrically conductive braided tubular body according to one example. In this example, device 10 is an implantable, medical electrical lead, referred to hereafter as "lead" 10. Lead 10 may be a cardiac sensing and pacing lead, for example, which may be used for delivering electrical signals to a patient's heart and/or sensing cardiac electrical signals produced by the patient's heart. In other examples, lead 10 may be used to sense electrical signals and/or deliver electrical stimulation therapy to the brain, skeletal muscle, smooth muscle, nerves, spinal cord or other tissues or organs of a patient.

Lead 10 includes a tubular elongated body 12 extending from a proximal end 14 to a distal end 16. Elongated body 12 defines one or more lumens through which electrical conductors may extend between proximal and distal ends 14 and 16. Elongated body 12 may carry one or more electrodes 30, 32 and 34 on or near distal end 16. In the example shown, a tip electrode 30, shown as an active fixation helical electrode is located on elongated body distal end 16. A ring electrode 32 may circumscribe elongated body 12 and be spaced proximally from tip electrode 30. Lead 10 may include one or more coil electrodes 34 configured for delivery of high voltage therapies, e.g., cardioversion/defibrillation (CV/DF) shock therapy. Coil electrode 34 is generally a higher surface area electrode than tip electrode 30 and ring electrode 32 which may be used in relatively lower voltage therapy delivery (e.g., cardiac pacing pulse delivery) and/or for sensing cardiac electrical signals. In various examples, lead 10 may include one or more electrodes which may be button, helical, hook, coil, ring or other types of electrodes, which may be carried anywhere along the length of lead body 12. Electrodes 30, 32 and 34 may be formed from, without limitation, titanium, tantalum, platinum, iridium or alloys thereof and may include a low polarizing coating, such as titanium nitride, iridium oxide, ruthenium oxide, platinum black among others.

Each electrode 30, 32 and 34 may be coupled to a respective electrical conductor extending through elongated body 12 to a proximal connector assembly 20 coupled to the proximal end 14 of elongated body 12. Proximal connector assembly 20 may include one or more electrical connectors, e.g., one or more ring connectors 24 and a pin connector 26. Each of the electrical connectors is electrically coupled to a respective electrode carried along the distal portion of elongated body 12 via an electrical conductor extending through elongated body 12. As described below, at least one of the distal electrodes 30, 32 or 34 may be electrically coupled to the braided tubular body as the electrical conductor (or portion thereof) coupling the electrode to the proximal connector assembly 20. Proximal connector assembly 20 may include a connector sleeve 22 for strain relief and coupling between elongated body 12 and the proximal connector assembly 20. The connector sleeve 22 may provide a fluid resistant seal between a connector bore of an implantable medical device, e.g., a pacemaker or implantable cardioverter defibrillator (ICD), configured to receive proximal connector assembly 20. Electrodes 30, 32 and 34 are thereby electrically coupled to circuitry, e.g., cardiac electrical signal sensing and therapy delivery circuitry of the pacemaker or ICD (or other medical device).

Elongated body 12 may be navigated along an internal body pathway, e.g., along a transvenous pathway or non-transvenous pathway, to position the distal end 16 at a cardiac pacing and sensing site, where distal tip electrode 30 may be screwed into tissue to anchor the elongated body distal end 16 at the pacing and sensing site. In other examples, the distal end 16 may include other fixation members, e.g., one or more tines, hooks, barbs, etc. for anchoring distal end 16 at the cardiac pacing and sensing site. In some examples, lead 10 is a transvenous pacing, sensing and cardioversion lead in which case distal tip electrode 30 may be implanted intracardially, e.g., within the ventricular or atrial myocardium. In other examples, lead 10 may be configured as a non-transvenous lead for implantation outside the cardiovascular system, e.g., supra- or substernally for pacing, sensing and/or delivery cardioversion/defibrillation shocks in an extra-cardiovascular medical device system. In still other examples, lead 10 may be placed along the spinal cord, advanced into the brain, advanced along or in skeletal muscle tissue, or advanced along other body tissues or organs for delivering an electrical stimulation therapy and/or sensing electrophysiological signals. Elongated body 12 may therefore traverse a tortuous pathway and/or undergo repetitive flexing within the beating heart and/or outside the heart due to patient body movement and motion.

According to the present disclosure, elongated body 12 includes a tubular, braided body 40 extending through at least a portion of elongated body 12. Tubular braided body 40 may be electrically conductive to provide an electrically conductive pathway along at least a portion of the elongated body 12 between proximal end 14 and distal end 12. The tubular braided body 40 is described below, e.g., in conjunction with FIGS. 2 and 3.

Tubular braided body 40 may define a central lumen through which one or more elongated members, such as inner insulative member 42 and/or electrical conductor(s) 44, may extend. For example, one or more elongated conductors 44, which may include one or more wire, coiled or cable conductors as examples, may extend between proximal connector assembly 20 and distal end 16. In the example shown, conductors 44 may include two electrically isolated and insulated elongated conductors extending from a respective connector of proximal connector assembly 20 to respective tip electrode 30 and ring electrode 32. The elongated conductor(s) 44 may extend within an insulative member 42 that provides electrical insulation between conductor(s) 44 and braided tubular body 40. In some examples, braided tubular body 40 may be electrically coupled to coil electrode 34 and a respective connector of proximal connector assembly 20 to provide electrical connection between coil electrode 34 and the proximal connector assembly 20.

Figure 2:
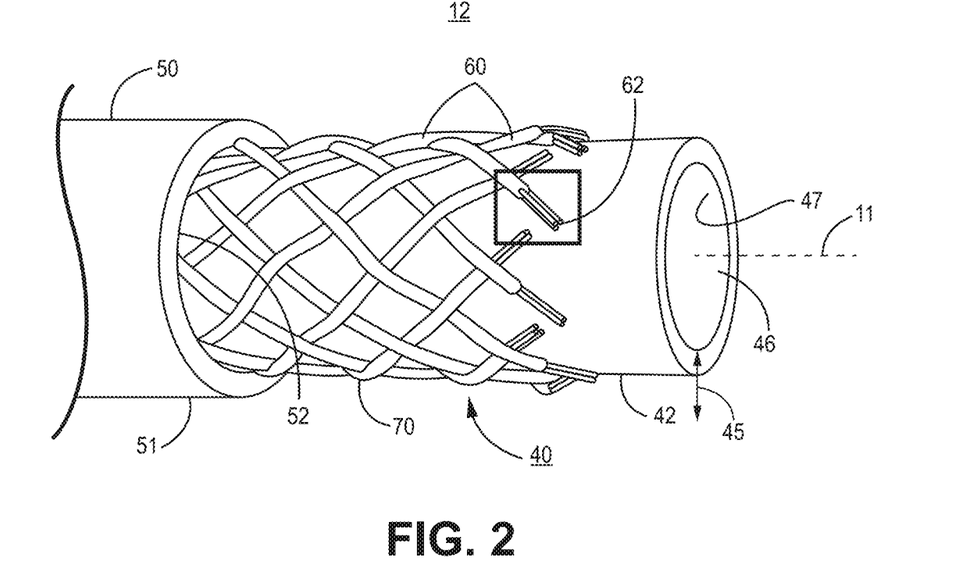
FIG. 2 is an enlarged view of a portion of the elongated body of the device of FIG. 1 according to one example.

FIG. 2 is an enlarged view of a portion of the elongated body 12 of lead 10 according to one example. Elongated body 12 is shown as a tubular body having an outer wall surface 51 and inner wall surface 47 separated by a wall thickness 45. Braided tubular body 40 extends between outer wall surface 52 and inner wall surface 47, within wall thickness 45. Elongated body 12 may include an outer tubular body 50 which may define an outer lumen 52 through which braided tubular body 40 extends. Outer tubular body 50 is flexible and electrically insulative and may include silicone, polyurethane or other medical grade, biocompatible polymer. Braided tubular body 40 may define a central lumen 46 through which one or more inner insulative members 44 and/or insulated electrical conductors may extend as described above in conjunction with FIG. 1. In FIG. 2, inner insulative member 42 is shown extending through central lumen 46 and is a flexible, tubular member that may provide electrical insulation between braided tubular body 40 and electrical conductors 44 extending through central lumen 46 as described above. Braided tubular body 40 may extend coaxially with outer tubular body 50, e.g., having a common central longitudinal axis 11, between outer wall surface 51 and inner wall surface 47, e.g., within wall thickness 45 between outer tubular body 50 and inner insulative member 42. Elongated member 12 including braided tubular body 40 may vary in diameter and is between 3 French and 8 French, inclusive, as examples.

Inner insulative member 42 may be formed from silicone, polyurethane, ethylene tetrafluoroethylene (ETFE), polytetrafluoroethylene (PTFE), or combinations thereof, as examples. In some examples, inner insulative member 42 is a PTFE material and may be, without limitation, 0.0010-0.0015 inches in wall thickness. In other examples, inner insulative member 42 may be a multi-lumen body defining multiple lumens, which may include one or more open lumens for delivery of a fluid or device there through and/or one or more lumens through which an electrical conductor extends. An elongated electrical conductor may extend through each lumen to a respective electrode, for example.

In some examples, inner insulative member 42 is an extruded member. Braided tubular body 40 may be braided over inner insulative member 42 by winding multi-filar cables 60 in opposing directions in an overlapping manner. Outer tubular body 50 may be extruded over the subassembly of braided tubular body 40 and inner insulative member 42 such that braided tubular body 40 is encapsulated by outer tubular body 50. Outer tubular body 50 may be a thermoplastic elastomer material, such as a polyether block amide or copolyester elastomer as examples. Outer tubular body 50 may wholly or partially encapsulate braided tubular body 40. For example, during an extrusion process, a thermoplastic material of outer tubular body 50 may flow around multi-filar cables 60 of braided tubular body 40 to encapsulate braided tubular body 40. In other examples, braided tubular body 40 may form a flush fit with inner insulative member 42 such that outer tubular body 50 partially encapsulates braided tubular body 40. The assembly of outer tubular body 50 and inner insulative member 42 defines wall thickness 45, through which braided tubular body 40 extends in a fluid tight fit in some examples. In other examples, braided tubular body 40 may form a relatively looser, non-fluid tight fit, with outer tubular body 50 and/or inner insulative member 42.

In other examples, the subassembly of the braided tubular body 40 braided around inner insulative member 42 may be threaded through the outer tubular body 50. Outer tubular body 50 may be a previously extruded body defining outer lumen 52 having a diameter sized to allow the subassembly of braided tubular body 40 and inner insulative member 42 to be threaded or advanced through lumen 52. A lubricating or anti-stick material such as isopropyl alcohol may be used to facilitate advancement of outer tubular body over the inner subassembly. In some examples, outer tubular body 50 may be dilated or swelled to partially encapsulate the braided tubular body and provide a tight fit between outer tubular body 50, braided tubular body 40 and inner insulative member 42. For example, when outer tubular body 50 includes silicone, heptane may be applied to swell the outer tubular body 50 to surround or partially encapsulate the braided tubular body. When outer tubular body includes polyurethane, tetrahydrofuran (THF) solvent may be used to swell or dilate outer tubular body 50 to tightly surround or partially encapsulate multi-filar cables 60.

In still other examples, inner insulative member 42 may be a mandrel over which braided tubular body 40 is assembled by winding cables 60 in opposing directions in an alternating, overlapping manner. Outer tubular body 50 may be threaded over the assembly of braided tubular body 40 and inner insulative member 42 and may be reflowed or melted to encapsulate braided tubular body 40, wholly or partially. The assembly of the braided tubular body 40 and inner insulative member 42 may be coated to provide a relatively smooth, reduced friction surface over which outer tubular body 50 is advanced over to assemble elongated body 12. The coating of the assembly of braided tubular body 40 and core insulation member 42 may be a polyether ether ketone coating, as an example. In other examples, outer tubular body 50 and inner insulative member 42 may be a unitary member encompassing braided tubular body 40 within wall thickness 45 through a combination of one or more extrusion, threading and thermoplastic reflow processes.

Depending on the medical application and overall desired stiffness of the elongated body 12, the braided tubular body 40 may be partially or fully encapsulated or not encapsulated at all but extending longitudinally over inner insulative member 42 and threaded through outer tubular body 50 (e.g., loose or press fit). For instance, when lead 10 is a cardiac pacing lead that is in the range of 4-5 French, the braided tubular body 40 may remain unencapsulated by the material of outer tubular body 50 to provide a relatively high flexibility lead body capable of withstanding repeated high bending stress. When lead 10 is a smaller diameter lead, for example 2-3 French, braided tubular body 50 may be fully encapsulated by outer tubular body 50, e.g., by reflowing outer tubular body 50 after threading over braided tubular body 40 to allow the thermoplastic material to flow around and encapsulate each cable of braided tubular body 40. Full encapsulation of the braided tubular body 40 may provide a desired stiffness of the smaller diameter lead for improving steerability and handling of the relatively small diameter lead. As the degree of encapsulation of braided tubular body 40 by the material of outer tubular body 50 increases, the stiffness of elongated body 12 may be increased in some examples.

Figure 3:
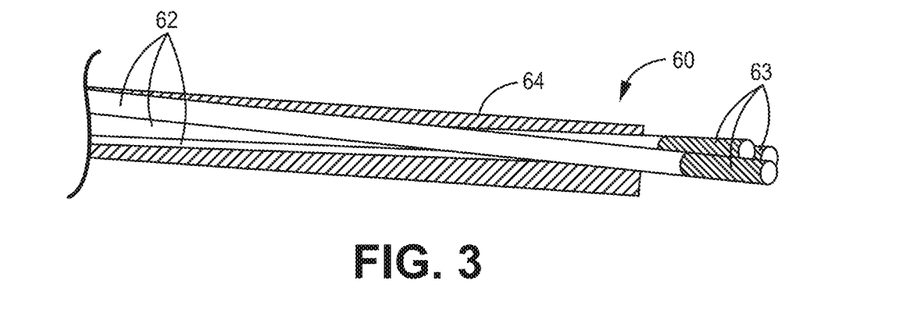
FIG. 3 is an enlarged view of an individual multi-filar cable included in the braided tubular body of FIG. 2.

Braided tubular body 40 includes multiple cables 60 braided together to form the tubular member 40. In the example shown, sixteen cables are braided to form tubular body 40, with eight cables extending helically in a clockwise direction around a central axis 11 of elongated body 12 and interwoven with eight cables wound to extend helically in the counter-clockwise direction. Each cable 60 includes multiple filars 62 as shown in FIG. 3. In other examples, fewer than 16 or more than 16 multi-filar cables may be braided to form braided tubular body 40. For example, braided tubular body 40 may include 8 to 32 multi-filar cables, with no limitation intended.

Furthermore, in some examples, braided tubular body 40 may include multiple multi-filar cables braided in combination with one or more other types of cables or wires. For example, half (or other portion) of the cables 60 may be multi-filar cables and the other half (or other portion) of the cables 60 may be single filar cables or wires. In examples including a combination of multi-filar cables and other types of cables or wires braided to form tubular body 40, all of the multi-filar cables may or may not be wound in the same direction.

FIG. 3 is an enlarged view of an individual multi-filar cable 60 included in braided tubular body 40. Each cable 60 shown in FIG. 2 may be a multi-filar cable including at least two filars or more, e.g., three filars 62 as shown. The filars 62 may be twisted as shown in FIG. 3 or extend parallel to one another along the length of cable 60, between its proximal and distal ends. While each multi-filar cable 60 is shown in FIG. 2 to be a trifilar cable, it is to be understood that each multi-filar cable 60 may have a different number of filars in some examples. For example, some of cables 60 may have three filars and some of cables 60 may have two filars or more than three filars. All filars 62 in a given cable 60 are electrically conductive in the examples presented here, however it is recognized that in other examples, some or all of filars 62 may be non-electrically conductive in some examples.

Each multi-filar cable 60 may include an insulating cable outer layer 64 surrounding and circumscribing inner electrically conductive filars 62. Cable outer layer 64 provides electrical insulation between the cables 60 of the braided tubular body 40, particularly at each pic crossing 70 (shown in FIG. 2) where the cables 60 cross one another to form the braided tubular body 40. Cable outer layer 64 may be a solution imidized (SI) polyimide coating, fluorinated polyimide, or polyether ether ether ketone (PEEK). In other examples, including acute applications that do not require chronic implantation (e.g., for more than one day) of the tubular body 12 within a patient, the cable outer layer 64 may be another thermoplastic material, such as polyethylene terephthalate (PET), polybutylene terephthalate (PBT), polyamide (PA), thermoplastic polyurethane (TPU), polyvinylidene fluoride (PVDF), polyetherimide (PEI), polysulfone, or polyimide-PTFE blends as examples. Exposure of cable outer layer 64 to a melting temperature during manufacturing, e.g., during reflowing of outer tubular body 50 is avoided. In some examples, all cables extending in a first direction, e.g., clockwise, around the central axis 11 of elongated body 12 include cable outer layer 64, and all cables extending in the second, opposite direction, e.g., counterclockwise, may include multiple insulated filars without having cable outer layer 64 circumscribing the multiple filars.

Each filar 62 may be an electrically conductive wire which may include an electrically conductive metal or alloy, such as steel, copper, platinum, iridium, tantalum, silver, nickel, cobalt, molybdenum or any combination or alloy thereof, as examples. In one example, each filar 62 is an MP35N® nickel-cobalt alloy wire with a silver core or a stainless steel core. Each filar 62 may include an insulative coating (not illustrated) over the electrically conductive wire. The insulative coating may be an SI polyimide coating in one example. In other examples, the filar coating may include a fluorinated polyimide or PEEK. However, each individual filar 62 is not individually insulated or coated in some examples. In this case, the multiple filars 62 may be electrically insulated by cable outer layer 64.

Braided tubular body 40 provides flexible reinforcement of elongated body 12, for example to prevent flexion that may cause fracture of outer tubular body 50. Braided tubular body 40 further provides torque transfer along the length of elongated body 12. When tip electrode 30 is a helical screw-in electrode as shown in FIG. 1, rotation of the proximal connector assembly 20, e.g., rotation of proximal pin connector 26, may cause rotation of helical tip electrode 30 to advance tip electrode 30 out of the elongated body distal end 16 and into tissue at the implant site. Braided tubular body 40 may improve the function of lead 10 by improving the transfer of rotational torque along the length of elongated body 12 compared to other types of electrical conductors, such as straight wires, cables or coiled conductors which may have a greater tendency to twist upon rotation of proximal end 14 of elongated body 12. Braided tubular body 40 may provide torque transfer for steering and advancing a distal end of a medical device, e.g., lead 10 shown in FIG. 1 and other catheters and lead examples referenced herein, and/or for delivery of an implantable medical device carried by the elongated body 12 to an implant site or implantation of a fixation member at the distal end of the elongated body 12.

The individual filars 63 of multi-filar cables 60 are able to slide in relation to one another when elongated body 12 is bending or flexed, providing relatively greater flexibility of elongated body 12 than when braided elongated body 40 includes braided single, solid wires each having the same cross-sectional area as each of the multi-filar cables 60. By increasing the number of filars in each cable 60, low resistance conduction of electrical signals, e.g., for sensing physiological signals, and/or high current conduction for therapy delivery, such as ablation therapy or cardioversion/defibrillation shocks, via braided tubular body 40 is achieved. The selected number of filars 62 in each cable of braided tubular body 40 to achieve a desired conductivity and the degree of encapsulation of the braided tubular body 40 by outer tubular body 50 to achieve a desired stiffness/flexibility enables a desired overall combination of stiffness or flexibility of lead 10 and electrical properties for signal conduction between proximal and distal ends of the elongated body 12.

With continued reference to FIGS. 2 and 3, cable outer layer 64 electrically and mechanically insulates the braided cables 60 at pic crossings 70. The cable outer layer 64 provided at the pic crossings 70 reduces the likelihood of fracture of the individual filars 62 at the pic crossings 70 where increased strain and frictional forces may occur. Electrical noise can be generated at pic crossings of uninsulated braided wires due to relative motion of the two wires crossing each other. Cable outer layer 64 may reduce electrical noise generation at pic crossings 70. Furthermore, the insulating coating on each individual filar 62 may reduce the likelihood of electrical noise generation and filar fracture, particularly at pic crossings 70, by electrically insulating each individual filar 62 from each other within multi-filar cable 60 and reducing friction between individual filars 62, allowing the filars 62 to more easily slide, shift, or move relative to each other during flexion or movement of elongated body 12.

The distal terminal end 63 of each individual filar 62 is uninsulated in some examples. Any insulating coating and/or cable outer layer 64 may be omitted or removed from distal terminal ends 63 to facilitate electrical connection between the filars 62 of cable 60 and an electrode or other sensor carried by the tubular body 12, e.g., an electrode of a pacemaker lead, ablation catheter, electrophysiological catheter, neurostimulation lead, cardiac monitoring lead, or the like. As described below, the distal terminal ends 63 of each cable 60 may be welded, crimped, bonded, press fit or otherwise coupled directly to an electrode or indirectly via a coupling member that is electrically coupled to the electrode to enable cable 60 to function as an electrical conductor carrying signals to and/or from an electrode. In some examples, an insulating coating on individual filars 63 may be removed due to heat during a laser welding process and does not have to be removed prior to electrical coupling to an electrode or other component.

Figure 4:
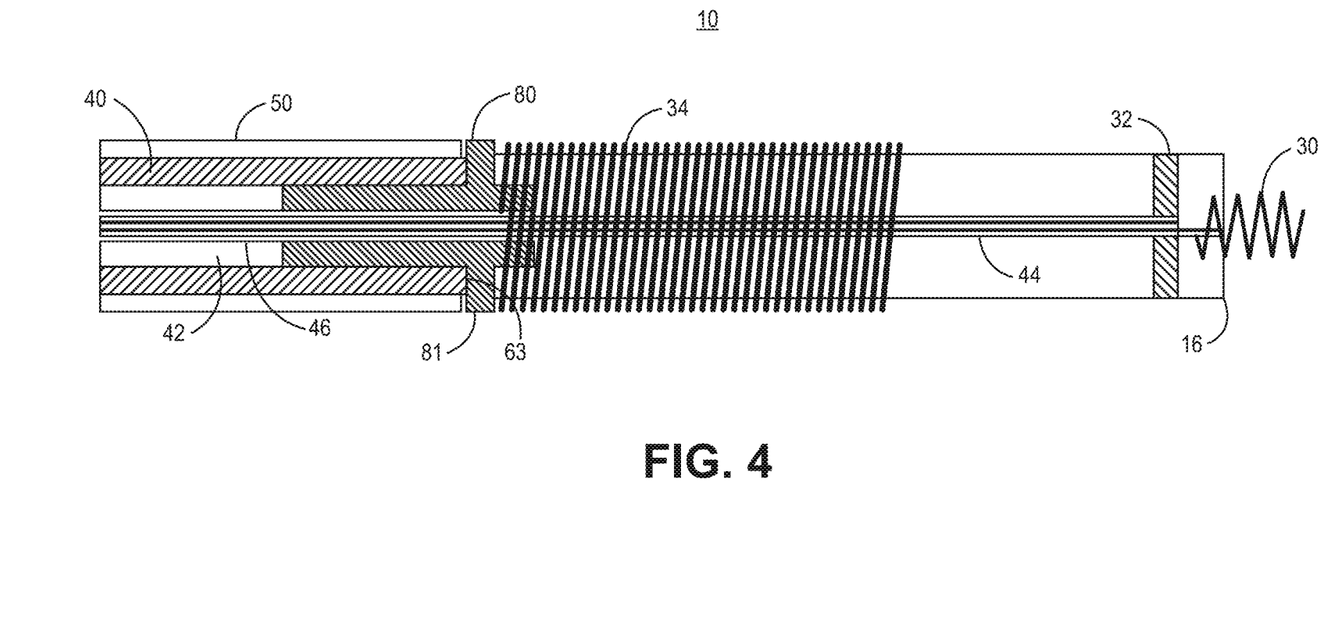
FIG. 4 is a conceptual diagram of a distal portion of a medical electrical lead.

FIG. 4 is a conceptual diagram of a distal portion of lead 10. In some examples, braided tubular body 40 is electrically coupled to an electrode carried by lead 10, e.g., at or adjacent distal end 16 of elongated body 12. In the example shown, braided tubular body 40 is electrically coupled to coil electrode 34, e.g., via a coupling member 80. Coupling member 80 may be a generally tubular member formed of an electrically conductive material, e.g., titanium, platinum, iridium, stainless steel, nickel, cobalt, or combinations or alloys thereof. Uninsulated distal ends 63 (shown in FIG. 3) of cables 60 included in braided tubular body 40 may be electrically and mechanically coupled to coupling member 80, e.g., by crimping, press fit between components and/or welding. A proximal portion of coil electrode 34 may be electrically and mechanically coupled to coupling member 80, e.g., along a distal portion of coupling member 80. Portions of coupling member 80 not electrically coupled to braided tubular body 40 or coil electrode 34 may be coated or enclosed by an electrically insulating layer, e.g., silicone, polyurethane, PEEK, ETFE, or PTFE.

Braided tubular body 40 may function has a high voltage conductor for coupling coil electrode 34 to high voltage therapy delivery circuitry in an ICD, for example. High voltage CV/DF shocks, which may be up to 40 Joules or higher, may be delivered via coil electrode 34. Braided tubular body 40, having multiple cables each having multiple filars, e.g., sixteen cables each having three filars for a total of 48 filars, provides the conductivity needed for delivering the required high voltage, CV/DF shock energy via coil electrode 34. The uninsulated distal, terminal filar ends 63 (illustrated in FIG. 3) of each cable 60 of braided tubular body 40 may be electrically coupled to coupling member 80, e.g., by laser welding the terminal ends of cables 60 to the coupling member 80. In other examples, distal terminal ends 63 of each cable 60 may be press fit between a coupling ring 81 and coupling member 80. In still other examples, the distal terminal ends 63 of all or at least a portion of cables 60 may be electrically tied together, e.g., by a metal band, wire, ring, ribbon or flexible circuit that is electrically coupled to electrode 34, directly or indirectly via coupling member 80.

While coil electrode 34 may be provided for delivering high voltage CV/DF shocks, coil electrode 34 may be used for sensing cardiac electrical signals and/or delivering relatively lower voltage pacing pulses. Braided tubular body 40 may therefore be electrically coupled to coil electrode 34 for providing electrical conductivity to proximal connector assembly 20 for sensing cardiac electrical signals and/or delivering electrical signals for therapy delivery. Furthermore, while electrode 34 is shown as a coil electrode, it is to be understood that other types of electrodes may be coupled to braided tubular body 40, either directly or indirectly via a coupling member, for example. For instance, electrode 34 may be provided as a segmented, ring, or other type of electrode that is electrically and mechanically coupled to braided tubular body 40, either directly or indirectly, e.g., via a coupling member 80.

Elongated conductors 44 extending through central lumen 46 may extend past the distal terminal end 41 of braided tubular body 40, to the distal ring electrode 32 (if present) and distal tip electrode 30. A described above, elongated conductors 44 may include two, insulated electrical conductors each electrically coupled to a respective one of the ring electrode 32 and the tip electrode 30 to provide electrical connection to a proximal connector of proximal connector assembly 20.

By electrically coupling braided tubular body 40 between a proximal connector and a distal electrode (or other sensor), the number of conductors required to extend through central lumen 46 is reduced. The conductive filars coated with an insulating layer included in each cable 60 promote flexibility while reducing the likelihood of fracture or electrical noise generation between filars at pic crossings of the braided tubular body 40. The insulating coating of each filar further protects and insulates the filars 62 during manufacturing and assembly methods that may involve high temperatures during an extrusion or polymer reflow process.

In other examples, a portion of cables 60 in braided tubular member 40 may be electrically coupled to a first electrode, and a second portion of cables 60 may be electrically coupled to a second electrode. The first and second electrodes may be electrically tied together to serve as a cathode or anode electrode, or the first and second electrodes may be electrically isolated from one another. For example, a first portion of the cables 60 of braided tubular body 40 may be coupled to coil electrode 34 and a second portion of the cables 60 may be electrically coupled to ring electrode 32, electrically isolated from coil electrode 34. In this example, a larger portion of cables 60 may be coupled to the high voltage coil electrode 34 to provide sufficient conductivity and a smaller portion of cables 60 may be coupled to low voltage ring electrode 32. Alternatively, the cables coupled to ring electrode 32 may have fewer filars than the cables coupled to coil electrode 34. When braided tubular body 40 terminates at coupling member 80 or coil electrode 34, a wire or flexible circuit may be electrically coupled to a portion of the cables 60 and extend distally to ring electrode 32 to provide electrical connection between distal ends 63 of cables 60 in braided tubular body 40 and ring electrode 32.

Figure 5:
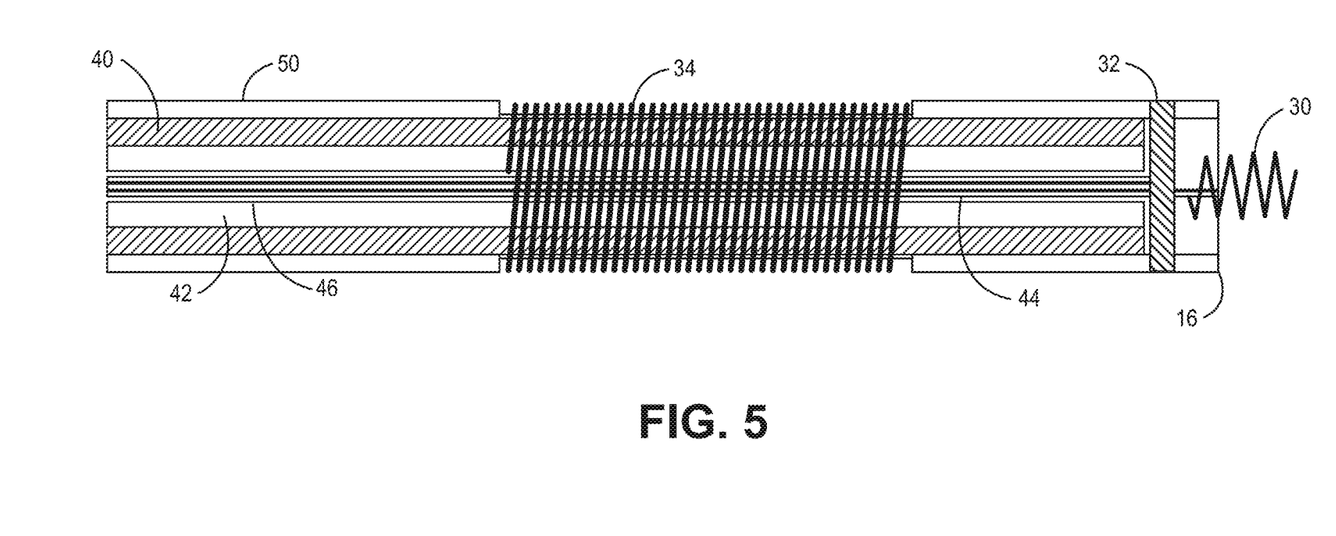
FIG. 5 is a conceptual diagram of a distal portion of a medical electrical lead according to another example.

FIG. 5 is a conceptual diagram of a distal portion of lead 10 according to another example. In the configuration shown in FIG. 4, braided tubular body 40 is shown to extend distally up to coil electrode 34. In other examples, braided tubular body 40 may extend further distally, e.g., all the way to distal end 16 of elongated body 12. In FIG. 5, braided tubular body 40 extends distally to elongated body distal end 16, through a lumen of coil electrode 34. In some examples, coil electrode 34 is electrically coupled to an uninsulated portion of braided tubular body 40 extending within the lumen of coil electrode 34. An inner surface of coil electrode 34 may be welded to an uninsulated outer surface of braided tubular body 40. Alternatively a coupling member or ring may reside between coil electrode 34 and braided tubular body 40 and provide electrical connection between the two, e.g., by a welded and/or press fit junction.

In still other examples, braided tubular body 40 may extend toward or all the way to elongated body distal end 16 and be electrically coupled to ring electrode 32 and/or tip electrode 30. Coil electrode 34 may be optional in this case, or if present coupled to a different electrical conductor extending through elongated body 12.

Figure 6:
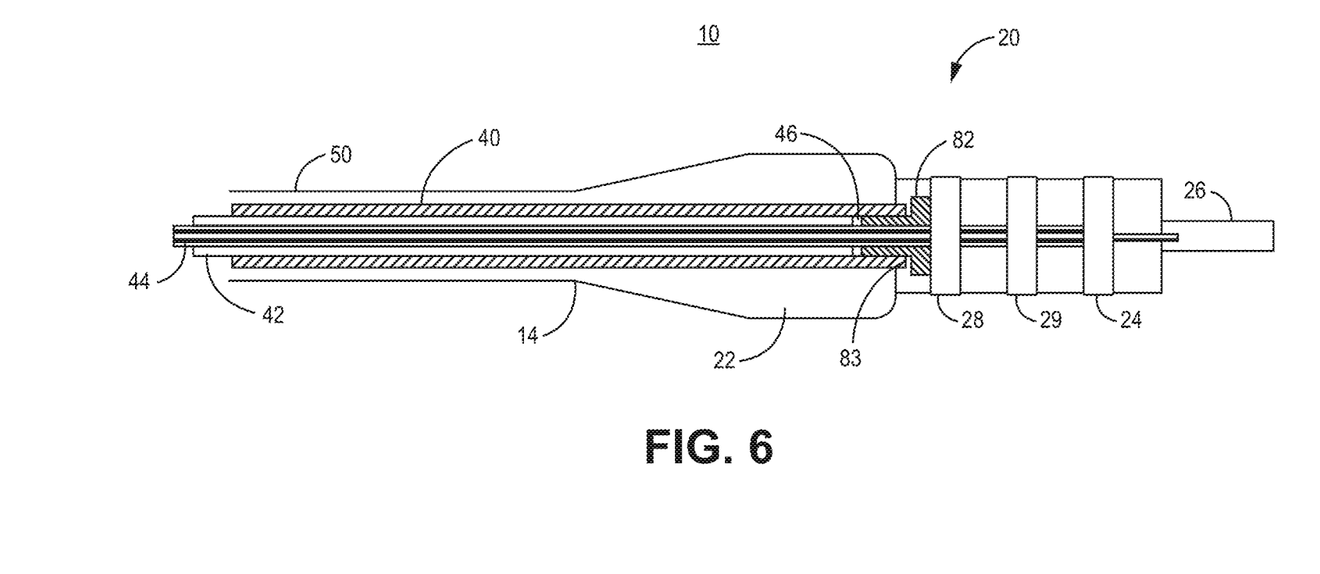
FIG. 6 is a conceptual diagram of a proximal portion of medical electrical lead according to one example.

FIG. 6 is a conceptual diagram of a proximal portion of lead 10. In this example, braided tubular body 40 extends proximally to elongated body proximal end 14 and may optionally extend further, into proximal connector assembly 20. Braided tubular body 40 is electrically coupled to a ring connector 28 of connector assembly 20. In the example shown, braided tubular body 40 is electrically and mechanically coupled to a proximal coupling member 82, e.g., by crimping, welding or other coupling methods. The proximal coupling member is electrically coupled to ring connector 28 which may be a high voltage connector that facilitates connection to therapy delivery circuitry of an ICD configured to receive proximal connector assembly 20. In one example, proximal connector assembly 20 may be an industry standard DF-4 connector having four inline connectors, three ring connectors 24, 28 and 19 and one pin connector 26. Two ring connectors 28 and 29 may be high voltage connectors for connecting CV/DF electrodes, such as electrode 34, to high voltage therapy delivery circuitry, and optionally cardiac electrical signal sensing circuitry and/or low voltage therapy delivery circuitry, in an ICD. The third ring connector 24 and the pin connector 25 may be low voltage connectors for connecting associated electrodes, e.g., distal tip electrode 30 and ring electrode 32 to low voltage pacing and sensing circuitry of the ICD. Each conductor included in elongated conductors 44 extending within central lumen 46 may extend proximally to respective ring connector 24 and pin connector 26 to provide electrical connection between the ring electrode 32 and tip electrode 30, respectively.

FIG. 6 is a conceptual diagram of one configuration of a proximal portion of a medical electrical lead 10 including braided tubular body 40 according to one example. Braided tubular body 40 is electrically coupled to a distal electrode, as described in conjunction with the examples of FIGS. 4 and 5. Braided tubular body 40 is electrically coupled at proximal terminal ends of cables 60 to proximal electrical connector 20. Numerous variations of a medical electrical lead may be conceived which include one or more electrodes carried by the elongated lead body and electrically coupled to a proximal connector assembly, where at least one electrode is electrically coupled to the braided tubular body 40 including multiple, insulated multi-filar cables as described above for providing electrical connection to a proximal connector assembly 20.

In some examples, the braided tubular body 40 extends from the proximal connector assembly 20 distally at least to a coil electrode, e.g., electrode 34, carried by the elongated body 20. The braided tubular body 40 may extend from a proximal coupling member 82 to a distal coupling member 80 (see FIG. 5) and be electrically and mechanically coupled to each of the proximal and distal coupling members 82 and 80 at uninsulated proximal terminal ends 83 and distal terminal ends 63, respectively, of the filars 62 of each multi-filar cable 60 forming braided tubular body 40. At the proximal terminal ends 83, braided tubular body may be electrically coupled to proximal coupling member 82 by welding, a press fit between components, crimping or other coupling means. The electrical connection of braided tubular body 40 to proximal coupling member 82 provides electrical connection to a connector ring 28, for example, and thereby to the electronic circuitry of a medical device.

Figure 7:
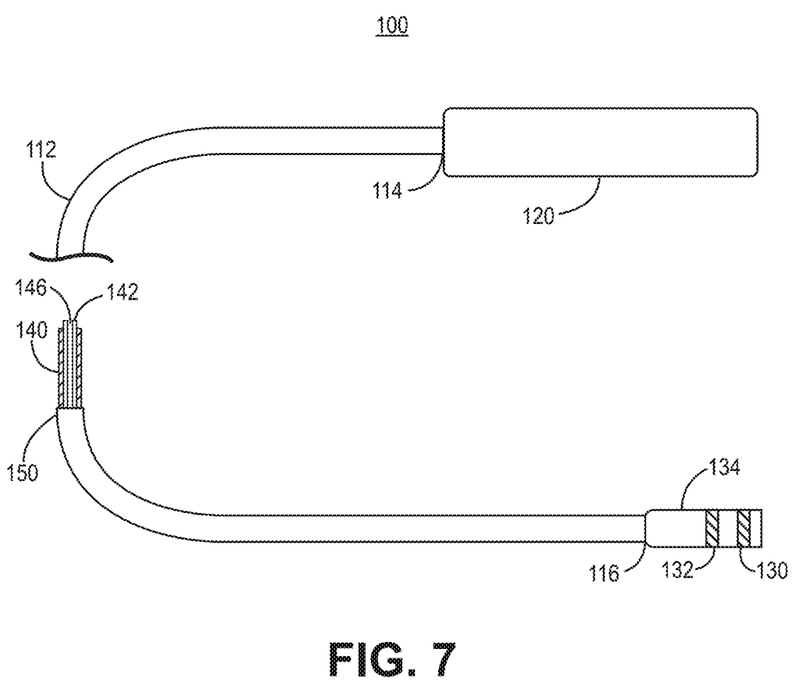
FIG. 7 is a conceptual diagram of an elongated medical device including a braided tubular body according to another example.

FIG. 7 is a conceptual diagram of an elongated medical device 100 including a braided tubular body according to another example. In this example, elongated medical device 100 is configured as a catheter, referred to hereafter as "catheter" 100. In various examples, catheter 100 may be a cardiac monitoring and/or therapy delivery catheter. For example, catheter 100 may carry one or more sensors for monitoring pressure, blood flow, cardiac electrical signals, heart sounds, oxygen saturation, or other physiological signals. Additionally or alternatively, catheter 100 may be configured to deliver a therapy, e.g., a pharmaceutical agent, cardiac pacing signals, ablation signals, etc., or deploying an implantable medical device for delivering a therapy. For instance, catheter 100 may be configured for delivering a leadless cardiac pacemaker, implantable sensor, coronary artery stent, angioplasty balloon, cyroablation balloon, radiofrequency ablation catheter or other device, which may be delivered transvenously to an implant site.

Cather 100 may include a proximal hub 120 and an elongated body 112. Elongated body 112 extends from proximal hub 120 at an elongated body proximal end 114 to an elongated body distal end 116. Elongated body 112 may enclose a central lumen 146. One or more tools or devices may be advanceable through elongated body 112 within central lumen 146, such as a guide wire, pull wire coupled to distal end 116, a medical electrical lead, or a drug delivery catheter, as examples. In other examples, central lumen 146 may be an open lumen providing fluid communication between proximal hub 120 and distal end 116 for fluid delivery. Elongated body 112 includes a braided tubular body 140 which may be insulated by an outer tubular body 50 and inner insulative member 142, which may define central lumen 146.

In some examples, elongated member 112 is coupled to a deployment bay 134 at distal end 116. Deployment bay 134 may be configured to retain an implantable medical device, such as a leadless cardiac pacemaker or implantable sensor, which is deployable from deployment bay 134 at an implant site. Deployment bay 134 is optional depending on the medical application for which catheter 100 is being used in that a device or fluid may be delivered through central lumen 146 and/or sensing or monitoring of physiological signals via catheter 100 may be performed without requiring deployment bay 134.

Catheter 100 may include one or more sensors, shown as electrodes 130 and 132, carried at or near distal end 116 of elongated member 112. In the example shown, electrodes 130 and 132 are shown distal to elongated body distal end 116, circumscribing deployment bay 134. However, in other examples, one or more electrodes or other sensors may be carried proximal to or on distal end 116 of elongated body 112. Electrodes 130 and 132 may be used for sensing electrophysiological signals and/or delivering electrical stimulation pulses or therapy at a target site. The distal end 116 of elongated body 112 may be navigated to a sensing site for positioning electrodes 132 and 134 for sensing electrophysiological signals, e.g., cardiac electrical signals produced by the patient's heart. One or more sensors for acquiring an electrophysiological signal and/or other physiological signal, e.g., pressure, acoustical, blood flow, oxygen saturation, temperature, etc., may be carried by elongated body 112 (or deployment bay 134) for positioning of the sensors(s) at an intended sensing site.

In some examples, braided tubular body 140 is electrically coupled to at least one sensor carried by elongated body 112. In the example shown, one or both of electrodes 130 and/or 134 may be electrically coupled to braided tubular body 140 to provide electrical connection between each of electrodes 130 and 132 and proximal hub 120. In other examples, one of electrodes 132 or 134 is electrically coupled to braided tubular body 140 and the other of electrodes 134 or 132 is electrically coupled to an elongated conductor which may extend through central lumen 146, e.g., as generally shown in FIG. 5 or FIG. 6.

As described above, braided tubular body 140 includes multiple cables, each including multiple filars, which are braided together to provide a flexible tubular body (as described in conjunction with FIGS. 2 and 3) that reinforces outer tubular body 150 and may provide electrical conduction between the proximal and distal ends 114 and 116 of catheter 100. One or more of the cables included in braided tubular body 140 may be electrically coupled to a given electrode 132 or 130. In some examples, all cables included in braided tubular body 140 are electrically coupled to at least one of electrodes 130 or 132. In other examples, fewer cables may be electrically coupled, e.g., half of the cables may be electrically coupled to one of electrodes 130 or 132. Electrical connection between at least a portion of the cables included in braided tubular body 140 may be made as generally described above, e.g., in conjunction with FIG. 5, by crimping, welding, press fit between a coupling member and the electrode or other methods. Braided tubular body 140 may be electrically coupled directly to the electrode 130 or 132 or indirectly via a coupling member.

When a different sensor is carried by catheter 100, in addition to or instead of electrodes 130 and 132, braided tubular body 140 may be configured to carry electrical signals to and from the sensor. For example, an electrical signal required to power the sensor may be conducted to the sensor and an electrical signal generated by the sensor, e.g., correlated to a change in pressure, flow, oxygen saturation or other signal being monitored depending on the type of sensor, may be conducted by braided tubular body 140 from the sensor to proximal hub 120. In some examples, one or more cables of braided tubular body 140 may carry an electrical signal to a sensor carried by catheter 100, and one or more cables may carry an electrical signal from the sensor back to proximal hub 120, which may be different cables or the same cables. In other words, a first portion of the multi-filar cables of braided tubular body 140 may transmit current to a physiological sensor and a second portion of the multi-filar cables of braided tubular body 140 may transmit current from the physiological sensor.

Cables of braided tubular body 140 may be encapsulated partially, wholly or not at all by outer tubular body 150 to provide a desired stiffness or flexibility of catheter 100. The individual filars of the multi-filar cables of braided tubular body 140 are able to slide in relation to one another as elongated body 112 is bending, providing relatively greater flexibility than a braided elongated body of single, solid wires of the same cross-sectional area as the multi-filar cables. By increasing the number of filars in each cable of braided tubular body, low resistance conduction of electrical signals, e.g., for sensing physiological signals, and/or high current conduction for therapy delivery, such as ablation therapy, is achieved. In this way, the number of filars in each cable of braided tubular body 140 and the degree of encapsulation of the braided tubular body by outer tubular body 150 enables a desired combination of stiffness or flexibility of the elongated body 112 and desired electrical properties for signal conduction.

Figure 8:
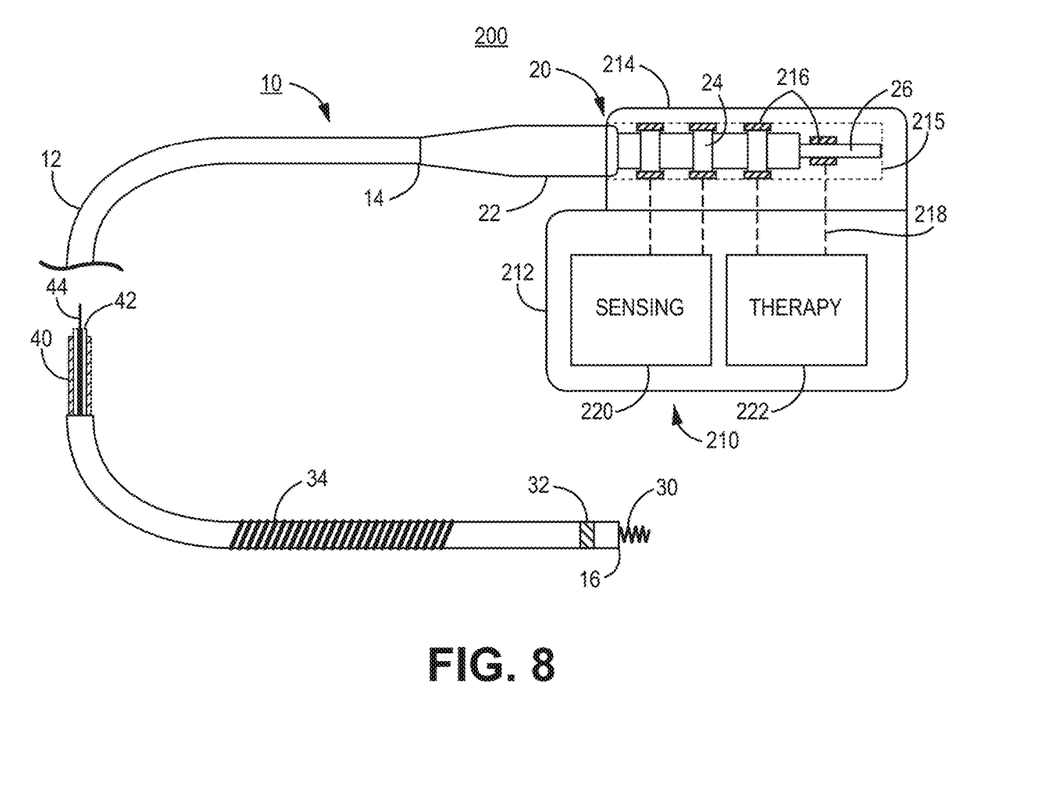
FIG. 8 is a conceptual diagram of a medical device system including a medical electrical lead having a braided tubular body according to one example.

FIG. 8 is a conceptual diagram of a medical device system 200 including a medical electrical lead 10 having a braided tubular body 40 according to one example. Lead 10 generally corresponds to the medical electrical lead 10 described above, e.g., in conjunction with FIG. 1. Lead 10 includes a proximal electrical connector 20 coupled to the proximal end 14 of the elongated tubular body 12. The braided tubular body 40 extends between the proximal end 14 and the distal end 16 of the elongated tubular body 12. The braided tubular body 40 includes a first plurality of cables winding in a first direction around the central axis of the elongated tubular body 12 and a second plurality of cables winding in a second direction, opposite the first direction around the central axis of the elongated tubular body 12. At least a portion of the first plurality of cables and the second plurality of cables are multi-filar cables with each of the multi-filar cables including multiple electrically conductive filars. All or at least a portion of the multi-filar cables of braided tubular body 40 are electrically coupled to one of the electrodes 30, 32 or 34 carried by the distal portion of elongated tubular body 12 and to one of the ring connectors 24 or pin connector 26 of the proximal electrical connector 20.

The medical device system 200 further includes a medical device 210 having a housing 212 and a connector block 214, sometimes referred to as a "header," coupled to the housing 212. Housing 212 encloses circuitry configured to sense physiological signals and/or deliver electrical stimulation therapy. For example, housing 212 may enclose a sensing circuit 220 configured to receive electrophysiological signals from electrodes 30, 32 and/or 34. Sensing circuit 220 may include various signal processing and analysis circuitry such as filters, amplifiers, analog-to-digital convertors, event detectors, comparators, rectifiers, etc. Medical device 210 may further include a therapy delivery circuit 222 which may include pulse generating circuitry, such as capacitor charging circuitry, holding and output capacitors, switching circuitry etc. configured to generate therapeutic electrical stimulation pulses and deliver the stimulation pulses via one or more of electrodes 30, 32 and 34 and in some cases housing 212. In some examples, the housing 212 may serve as an electrode paired with electrodes carried by lead 10.

The connector block 214 includes a connector bore 215 configured to receive the proximal connector assembly 20. Electrical contacts 216 reside along connector bore 215 in positions that align with ring connectors 24 and pin connector 26 when the proximal connector assembly 20 is fully inserted into connector bore 215. Each electrical contact 216 is electrically coupled to circuitry within housing 212, e.g., to at least one of the therapy delivery circuit 222 and/or the sensing circuit 220 via various insulated electrical feedthroughs 218 that cross housing 212 for electrically connecting electrodes 30, 32 and 34 to the therapy delivery circuit 222 and/or the sensing circuit 220 when the proximal connector assembly 20 is received by (fully inserted into) the connector bore 215.

Feedthroughs 218 are shown conceptually between contacts 216 and sensing circuit 220 and therapy delivery circuit 222 without necessarily illustrating exact or all connections possible between contacts 216 and internal medical device circuitry that may exist. In the example of lead 10, for instance, tip electrode 30 may be coupled to pin connector 26 which may be switchably coupled to both therapy delivery circuit 222 and sensing circuit 220 via feedthroughs 218. Ring electrode 32 and coil electrode 34 may each be coupled to a respective ring connector 24 and switchably coupled to both sensing circuit 220 and therapy delivery circuit 222 via feedthroughs 218. The particular electrical connections made between proximal connector assembly contacts 216 and various feedthroughs 218 and internal electronic circuitry within housing 212 will depend on the particular sensing and stimulation needs for a particular medical application. In some examples, medical device 210 is a cardiac pacemaker. In other examples medical device 210 is an implantable cardioverter defibrillator (ICD) and coil electrode 34 is a high voltage cardioversion/defibrillation electrode that is electrically coupled to braided tubular body 40 and therapy delivery circuit 222 via proximal connector assembly 20, connector block contacts 216 and feedthroughs 218. In general, braided tubular body 40 may conduct signals to and/or from one or more of electrodes 30, 32 and/or 34 from and/or to circuitry enclosed by housing 212.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

ILLUSTRATIVE EMBODIMENTS

Embodiment 1. A medical device, comprising:
an elongated tubular body having a proximal end, a distal end and a central axis;
a braided tubular body extending between the proximal end and the distal end of the elongated tubular body, the braided tubular body comprising:
a first plurality of cables winding in a first direction around the central axis of the elongated tubular body; and
a second plurality of cables winding in a second direction opposite the first direction around the central axis of the elongated tubular body;
wherein at least a portion of the first plurality of cables and the second plurality of cables are multi-filar cables, each multi-filar cable comprising a first plurality of filars.

Embodiment 2. The medical device of embodiment 1, wherein all of the first plurality of cables are multi-filar cables, each multi-filar cable of the first plurality of cables comprising the first plurality of filars.

Embodiment 3. The medical device of any of embodiments 1 to 2, wherein each one of the second plurality of cables being a multi-filar cable, each multi-filar cable of the second plurality of cables comprising a second plurality of filars.

Embodiment 4. The medical device of any of embodiments 1 to 3, wherein the first plurality of filars being a different number of filars than the second plurality of filars.

Embodiment 5. The medical device of any of embodiments 1-4, wherein each filar of the multi-filar cables comprises an electrically conductive wire having an electrically insulative coating.

Embodiment 6. The medical device of any of embodiments 1-5, wherein:
the elongated tubular body includes an outer tubular body and an inner insulating member, the outer tubular body and the inner insulating member defining a wall thickness of the elongated body; and
the braided tubular body extends within the wall thickness coaxially with the outer tubular body and the inner insulating member.

Embodiment 7. The medical device of any of embodiments 1 to 6, wherein the outer tubular body encapsulates the cables of the braided tubular body.

Embodiment 8. The medical device of any of embodiments 1 to 7, wherein the elongated tubular body has a central axis, an inner wall and an outer wall, the inner wall and the outer wall separated by a wall thickness,
the braided tubular body extending coaxially with the elongated body and within the wall thickness of the elongated body, between the inner wall and the outer wall.

Embodiment 9. The medical device of any of embodiments 1 to 8, wherein each of the multi-filar cables comprises an outer electrically insulating layer that circumscribes the first plurality of filars.

Embodiment 10. The medical device of any of embodiments 1 to 9, further comprising:
a sensor; and
a proximal connector coupled to the proximal end of the elongated tubular body;
wherein the braided tubular body extends between the sensor and the proximal connector and is electrically coupled to the sensor and to the proximal connector.

Embodiment 11. The medical device of any of embodiments 1 to 10, further comprising:
an electrode carried by the elongated tubular body;
a proximal connector coupled to the proximal end of the elongated tubular body;
wherein the braided tubular body extends between the electrode and the proximal connector and is electrically coupled to the electrode and to the proximal connector.

Embodiment 12. The medical device of embodiment 11, wherein the electrode comprises an elongated coil electrode circumscribing an outer diameter of the elongated body.

Embodiment 13. The medical device of any of embodiments 1 to 12, wherein:
each one of the first plurality of cables and the second plurality of cables being a trifilar cable; and
each filar comprising:
a nickel-cobalt alloy wire having a core comprising at least one of silver and stainless steel; and
a polyimide coating circumscribing the nickel-cobalt alloy wire.

Embodiment 14. The medical device of any of embodiments 1 to 13, further comprising:
a first electrode coupled to the distal end of the elongated tubular body;
a second electrode carried by the elongated tubular body and spaced apart proximally from the first electrode;
a proximal connector assembly coupled to the proximal end of the elongated tubular body and comprising a first connector and a second connector;
the elongated tubular body comprising a central lumen extending through the braided tubular body;
an elongated electrical conductor extending through the central lumen of the elongated tubular body from the first electrode to the proximal connector assembly, the elongated electrical conductor being electrically coupled to the first electrode and to the first connector; and the braided tubular body extending from the second electrode to the proximal connector assembly, the braided tubular body being electrically coupled to the second electrode and to the second connector of the proximal connector assembly.

Embodiment 15. The medical device of any of embodiments 1 to 13, further comprising:
a first electrode carried by the elongated tubular body; and
a first proximal electrical connector coupled to the proximal end of the elongated tubular body;
wherein a first portion of the multi-filar cables are electrically coupled to the first electrode and the first proximal electrical connector.

Embodiment 16. The medical device of embodiment 15, further comprising:
a second electrode carried by the elongated tubular body;
a second proximal electrical connector coupled to the proximal end of the elongated tubular body;
wherein a second portion of the multi-filar cables different than the first portion of the multi-filar cables are electrically coupled to the second electrode and the second proximal electrical connector.

Embodiment 17. The medical device of any of embodiments 1 to 16, wherein:
each of the first plurality of filars of each of the multi-filar cables comprises an electrically conductive wire having a terminal distal end; and
each of the multi-filar cables comprises an outer insulating layer that terminates proximal to the terminal distal ends.

Embodiment 18. The medical device of any of embodiments 1 to 17 1, wherein the first plurality of filars of each of the multi-filar cables are twisted.

Embodiment 19. An implantable medical electrical lead, comprising:
an elongated tubular body having a proximal end, a distal end and a central axis;
an electrode carried by the elongated tubular body;
a proximal electrical connector coupled to the proximal end of the elongated tubular body;
a braided tubular body extending between the proximal end and the distal end of the elongated tubular body, the braided tubular body comprising:
a first plurality of cables winding in a first direction around the central axis of the elongated tubular body; and
a second plurality of cables winding in a second direction opposite the first direction around the central axis of the elongated tubular body;
wherein at least a portion of the first plurality of cables and the second plurality of cables are multi-filar cables, each multi-filar cable comprising a plurality of electrically conductive filars, and
at least a portion of the multi-filar cables being electrically coupled to the electrode and to the proximal electrical connector.

Embodiment 20. An implantable catheter, comprising:
an elongated tubular body having a proximal end, a distal end and a central axis;
an electrode carried by the elongated tubular body;
a proximal electrical connector coupled to the proximal end of the elongated tubular body;
a braided tubular body extending between the proximal end and the distal end of the elongated tubular body, the braided tubular body comprising:

a first plurality of cables winding in a first direction around the central axis of the elongated tubular body; and
a second plurality of cables winding in a second direction opposite the first direction around the central axis of the elongated tubular body;
wherein at least a portion of the first plurality of cables and the second plurality of cables are multi-filar cables, each multi-filar cable comprising a plurality of electrically conductive filars, and
at least a portion of the multi-filar cables being electrically coupled to the electrode and to the proximal electrical connector.

Embodiment 21. An implantable medical device system, comprising:
a medical electrical lead comprising:
an elongated tubular body having a proximal end, a distal end and a central axis;
an electrode carried by the elongated tubular body;
a proximal electrical connector coupled to the proximal end of the elongated tubular body; and
a braided tubular body extending between the proximal end and the distal end of the elongated tubular body, the braided tubular body comprising:
a first plurality of cables winding in a first direction around the central axis of the elongated tubular body; and
a second plurality of cables winding in a second direction opposite the first direction around the central axis of the elongated tubular body;
wherein at least a portion of the first plurality of cables and the second plurality of cables are multi-filar cables, each multi-filar cable comprising a plurality of electrically conductive filars, and
at least a portion of the multi-filar cables being electrically coupled to the electrode and to the proximal electrical connector; and
a medical device comprising:
a housing enclosing at least one of a therapy delivery circuit and a sensing circuit; and
a connector assembly coupled to the housing, the connector assembly comprising:
a connector bore configured to receive the proximal electrical connector; and
an electrical contact residing within the connector bore, the electrical contact electrically coupled to the at least one of the therapy delivery circuit and the sensing circuit for electrically connecting the electrode to the at least one of the therapy delivery circuit and the sensing circuit when the proximal electrical connector is received by the connector bore.

What is claimed is:
1. A medical device, comprising:
an elongated tubular body having a proximal end, a distal end, and a central axis; and
a braided tubular body extending between the proximal end and the distal end of the elongated tubular body, the braided tubular body comprising:
a first plurality of cables winding in a first direction around the central axis of the elongated tubular body; and
a second plurality of cables winding in a second direction opposite the first direction around the central axis of the elongated tubular body, wherein the second plurality of cables is interwoven with the first plurality of cables such that the first plurality of cables and the second plurality of cables cross one another at a plurality of pic crossings;

wherein at least a portion of the first plurality of cables and the second plurality of cables are multi-filar cables, each multi-filar cable comprising a first plurality of filars, wherein each of the multi-filar cables comprises an outer electrically insulating layer that circumscribes the first plurality of filars, wherein the outer electrically insulating layer of each of the multi-filar cables electrically insulates each multi-filar cable from other cables of the first and second pluralities of cables at least at the pic crossings, and wherein each filar of the multi-filar cables comprises an electrically conductive wire having an electrically insulative coating.

2. The medical device of claim 1, wherein all of the first plurality of cables are multi-filar cables, each multi-filar cable of the first plurality of cables comprising the first plurality of filars.

3. The medical device of claim 1, wherein each one of the second plurality of cables is a multi-filar cable, each multi-filar cable of the second plurality of cables comprising a second plurality of filars.

4. The medical device of claim 3, wherein the first plurality of filars comprise a different number of filars than the second plurality of filars.

5. The medical device of claim 1, wherein:
the elongated tubular body includes an outer tubular body and an inner insulating member, the outer tubular body and the inner insulating member defining a wall thickness of the elongated body; and
the braided tubular body extends within the wall thickness coaxially with the outer tubular body and the inner insulating member.

6. The medical device of claim 5, wherein the outer tubular body encapsulates the cables of the braided tubular body.

7. The medical device of claim 1, wherein the elongated tubular body has an inner wall and an outer wall, the inner wall and the outer wall separated by a wall thickness, the braided tubular body extending coaxially with the elongated body and within the wall thickness of the elongated body, between the inner wall and the outer wall.

8. The medical device of claim 1, further comprising:
a sensor; and
a proximal connector coupled to the proximal end of the elongated tubular body;
wherein the braided tubular body extends between the sensor and the proximal connector and is electrically coupled to the sensor and to the proximal connector.

9. The medical device of claim 1, further comprising:
an electrode carried by the elongated tubular body; and
a proximal connector coupled to the proximal end of the elongated tubular body;
wherein the braided tubular body extends between the electrode and the proximal connector and is electrically coupled to the electrode and to the proximal connector.

10. The medical device of claim 9, wherein the electrode comprises an elongated coil electrode circumscribing an outer diameter of the elongated body.

11. The medical device of claim 1, wherein each one of the first plurality of cables and the second plurality of cables is a trifilar cable;
wherein each filar comprises a nickel-cobalt alloy wire having a core comprising at least one of silver and stainless steel; and
wherein the electrically insulative coating on each filar comprises a polyimide coating circumscribing the nickel-cobalt alloy wire.

12. The medical device of claim 1, further comprising:
a first electrode coupled to the distal end of the elongated tubular body;
a second electrode carried by the elongated tubular body and spaced apart proximally from the first electrode;
a proximal connector assembly coupled to the proximal end of the elongated tubular body and comprising a first connector and a second connector;
the elongated tubular body comprising a central lumen extending through the braided tubular body;
an elongated electrical conductor extending through the central lumen of the elongated tubular body from the first electrode to the proximal connector assembly, the elongated electrical conductor being electrically coupled to the first electrode and to the first connector; and
the braided tubular body extending from the second electrode to the proximal connector assembly, the braided tubular body being electrically coupled to the second electrode and to the second connector of the proximal connector assembly.

13. The medical device of claim 1, further comprising:
a first electrode carried by the elongated tubular body; and
a first proximal electrical connector coupled to the proximal end of the elongated tubular body;
wherein a first portion of the multi-filar cables is electrically coupled to the first electrode and the first proximal electrical connector.

14. The medical device of claim 13, further comprising:
a second electrode carried by the elongated tubular body; and
a second proximal electrical connector coupled to the proximal end of the elongated tubular body;
wherein a second portion of the multi-filar cables different than the first portion of the multi-filar cables are electrically coupled to the second electrode and the second proximal electrical connector.

15. The medical device of claim 1, wherein each of the first plurality of filars of each of the multi-filar cables has a terminal distal end.

16. The medical device of claim 1, wherein the first plurality of filars of each of the multi-filar cables are twisted.

17. An implantable medical electrical lead, comprising:
an elongated tubular body having a proximal end, a distal end, and a central axis;
an electrode carried by the elongated tubular body;
a proximal electrical connector coupled to the proximal end of the elongated tubular body; and
a braided tubular body extending between the proximal end and the distal end of the elongated tubular body, the braided tubular body comprising:
a first plurality of cables winding in a first direction around the central axis of the elongated tubular body; and
a second plurality of cables winding in a second direction opposite the first direction around the central axis of the elongated tubular body, wherein the second plurality of cables is interwoven with the first plurality of cables;
wherein at least a portion of the first plurality of cables and the second plurality of cables are multi-filar cables, each multi-filar cable comprising a plurality of electrically conductive filars, and at least a portion of the multi-filar cables being electrically coupled to the electrode and to the proximal electrical connector, wherein each of the multi-filar cables comprises an outer electrically insulating layer that circumscribes a first plurality of filars, and wherein each filar of the multi-filar cables comprises an electrically conductive wire having an electrically insulative coating.

18. An implantable catheter, comprising:
an elongated tubular body having a proximal end, a distal end, and a central axis;
an electrode carried by the elongated tubular body;
a proximal electrical connector coupled to the proximal end of the elongated tubular body; and
a braided tubular body extending between the proximal end and the distal end of the elongated tubular body, the braided tubular body comprising:
  a first plurality of cables winding in a first direction around the central axis of the elongated tubular body; and
  a second plurality of cables winding in a second direction opposite the first direction around the central axis of the elongated tubular body, wherein the second plurality of cables is interwoven with the first plurality of cables;
  wherein at least a portion of the first plurality of cables and the second plurality of cables are multi-filar cables, each multi-filar cable comprising a plurality of electrically conductive filars, and at least a portion of the multi-filar cables being electrically coupled to the electrode and to the proximal electrical connector, wherein each of the multi-filar cables comprises an outer electrically insulating layer that circumscribes a first plurality of filars, and wherein each filar of the multi-filar cables comprises an electrically conductive wire having an electrically insulative coating.

19. An implantable medical device system, comprising:
a medical electrical lead comprising:
  an elongated tubular body having a proximal end, a distal end, and a central axis;
  an electrode carried by the elongated tubular body;
  a proximal electrical connector coupled to the proximal end of the elongated tubular body; and
  a braided tubular body extending between the proximal end and the distal end of the elongated tubular body, the braided tubular body comprising:
    a first plurality of cables winding in a first direction around the central axis of the elongated tubular body; and
    a second plurality of cables winding in a second direction opposite the first direction around the central axis of the elongated tubular body, wherein the second plurality of cables is interwoven with the first plurality of cables;
    wherein at least a portion of the first plurality of cables and the second plurality of cables are multi-filar cables, each multi-filar cable comprising a plurality of electrically conductive filars, and at least a portion of the multi-filar cables being electrically coupled to the electrode and to the proximal electrical connector, wherein each of the multi-filar cables comprises an outer electrically insulating layer that circumscribes a first plurality of filars, and wherein each filar of the multi-filar cables comprises an electrically conductive wire having an electrically insulative coating; and
a medical device comprising:
  a housing enclosing at least one of a therapy delivery circuit and a sensing circuit; and
  a connector assembly coupled to the housing, the connector assembly comprising:
    a connector bore configured to receive the proximal electrical connector; and
    an electrical contact residing within the connector bore, the electrical contact electrically coupled to the at least one of the therapy delivery circuit and the sensing circuit for electrically connecting the electrode to the at least one of the therapy delivery circuit and the sensing circuit when the proximal electrical connector is received by the connector bore.

20. The medical device of claim 1, wherein the braided tubular body provides torque transfer along the length of the elongated body.

* * * * *